United States Patent [19]

Guillou et al.

[11] Patent Number: Plant 7,721

[45] Date of Patent: Nov. 26, 1991

[54] VARIETY OF GERANIUM NAMED YVETTE

[75] Inventors: Jacques Guillou; Bernard Guillou; Maurice Guillou, all of Saint-Malo, France

[73] Assignee: Etablissement Guillou Freres Jacques, Bernard et Maurice, Saint-Malo, France

[21] Appl. No.: 572,442

[22] Filed: Aug. 27, 1990

[51] Int. Cl.[5] ..... A01H 5/00

[52] U.S. Cl. ..... Plt./68

[58] Field of Search ..... Plt./68

*Primary Examiner*—James R. Feyrer

*Attorney, Agent, or Firm*—Webb, Burden, Ziesenheim & Webb

[57] ABSTRACT

A new and distinct Geranium variety is an improvement over those ivy Geraniums presently available on the market. The overall plant structure and habit with the lavender bloom and richer foliage color brings about that improvement. Cutting production and ease of rooting are also improved.

1 Drawing Sheet

BACKGROUND OF THE INVENTION

The present invention comprises a new and distinct cultivar of *Pelargonium*×*peltatum* known by the varietal name Yvette (Oglevee No. 7034, French No. 416, Guililas). The new variety was discovered in a selective breeding program by Messrs. Jacques, Maurice and Bernard Guillou. The new variety is a selection from a crossing of No. 315 by No. 280.

The new cultivar was discovered in July 1984 at 55 rue Godard, 35400 Saint-Malo, France, was first asexually reproduced by cuttings following its discovery at Saint-Malo, France and more recently has been repeatedly asexually reproduced by cuttings at Oglevee Ltd. in Connellsville, Pa. It has been found to retain its distinctive characteristics through successive propagations.

The new cultivar when grown in a glass greenhouse in Connellsville, Pa. using full light 60° F. (night), 68° F. (day), and 71° F. (vent) and grown in a soilless media with constant fertilizer at 200 to 250 parts per million of nitrogen and potassium has a response time from a rooted cutting to a flowering plant in a 10 centimeter pot of 6 weeks.

DESCRIPTION OF THE DRAWING

The accompanying drawing illustrates a new cultivar, the color being as nearly true as possible with color illustrations of this type.

DESCRIPTION OF THE NEW PLANT

The following detailed description sets forth the characteristics of the new cultivar. The data which define these characteristics were collected by asexual reproductions carried out by Oglevee Ltd. in Connellsville, Pa. Plants were started as rooted cuttings which were potted on Aug. 1, 1989 and flowered on Sept. 15, 1989. The plant histories were taken on plants blossomed under full light in a greenhouse and color readings were taken indoors under 200–220 foot candles of cool, white fluorescent light. Color references are primarily to the R.H.S. Colour Chart of The Royal Horticultural Society of London.

THE PLANT

Classification:

*Botanical.*—*Pelargonium*×*peltatum.*

*Commercial.*—Ivy Geranium.

Form: Cascading mound habit.

Height: 17 cm above media surface.

Growth: Free branching, upright mound with cascading side growth, free and early flowering.

Strength: Holds an upright mound shape while allowing outer branches to cascade over the sides of the pot.

Foliage: Stalked leaf attachment, little or no zone present.

Leaves:

- *Size.*—5.5–8.5 cm across.
- *Shape.*—Reniform; cordate base.
- *Margin.*—Pedately lobed.
- *Texture.*—Leathery, smooth, reflective.
- *Color.*—Top: Green Group 137A. Bottom: Yellow-Green Group 146A.
- *Ribs and veins.*—Venation palmate; Color Yellow-Green Group 146B.

Petioles: 3–6.5 cm in length, Yellow-Green Group 146B.

Stem:

- *Color.*—Yellow-Green Group 146B.
- *Internodes.*—2.5–5 cm in length.

THE BUD

Shape: Upright; semi-hemispherical cluster.

Size: 1.5–3.0 cm across.

INFLORESCENCE

Blooming habit: Upright and continues; semi-hemispherical; some shattering present.

Size: 7–9.0 cm across when fully open.

Borne: Florets on pedicel, pedicel on peduncle; umbel; 4–6.5 cm above foliage.

Florets:

- *Form.*—Flat to slightly cupped.
- *Color.*—Top: Purple Group 77C, venation on upper three petals; Red-Purple Group 71A. Bottom: Purple Group 75C.
- *Petals.*—9–19 in number; separate; not united; margin entire.
- *Size.*—4.5–5 cm across when fully expanded.

*Texture and appearance.*—Smooth; from a distance the color appears a light purple or lavender with a blotch of maroon near the center.

Petaloids:

*Quantity.*—Varies from 1-6.

*Shape.*—Elongated, twisted some with anther attached.

*Color.*—Varies from as light as Purple Group 75C to as dark as Purple Group 75B.

Pedicel:

*Length.*—1.5-2.5 cm in length.

*Color.*—Yellow-Green Group 146B.

Peduncle:

*Length.*—7.0-15.5 cm in length, arises from the node opposite leaf petiole.

*Color.*—Yellow-Green Group 146B.

Disease resistance: Not known.

Lasting quality: This variety improves upon the current ivy geraniums in both heat tolerance and shatter resistance.

REPRODUCTIVE ORGANS

Stamens:

*Anthers.*—Approximately 3 mm in length.

*Filaments.*—9 to 11 mm in lengths; white to a light pink.

*Pollen.*—Golden brown.

Pistils:

*Number.*—One; 6 to 7 part stigma.

*Length.*—9-11 mm.

*Stigma.*—6 to 7 parted; Red-Purple.

*Style.*—3-5 mm in length, light pink in color.

Ovaries: Superior; pale green; very pubescent; 4-7 mm in length; 2-3 mm across.

Fruit: None observed.

This new variety is an improvement over the most comparable variety Cornell (U.S. Pat. No. 3,888). This variety has a more attractive lavender bloom color and richer foliage color than Cornell. The plant is also of fuller habit. Cutting production and ease of rooting are also improved over the variety Cornell. The overall plant structure and habit along with the lavender bloom brings a substantial improvement to the ivy Geranium market.

I claim:

1. A new and distinct ivy Geranium as shown and described herein.

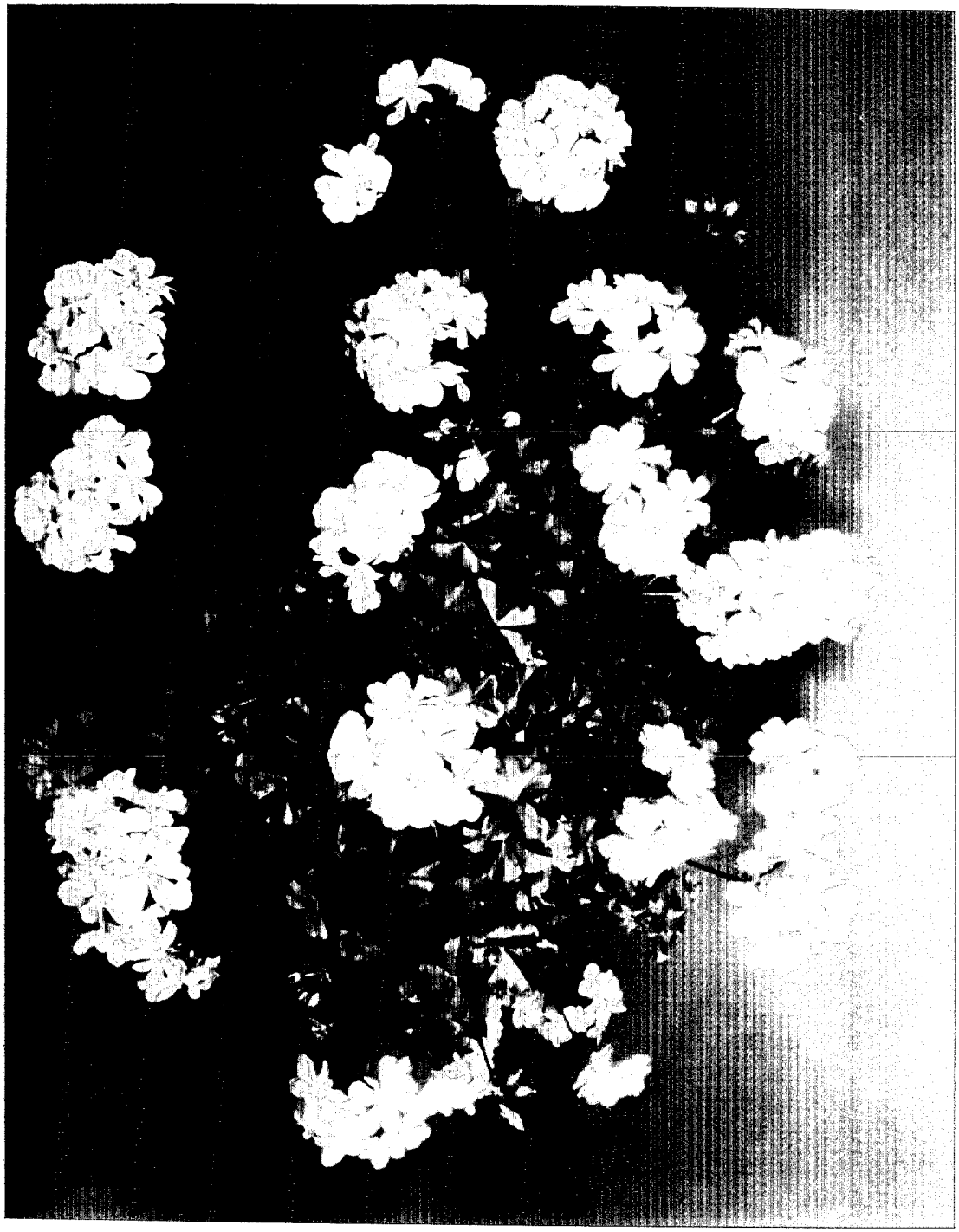

* * * * *